United States Patent
Malec et al.

(10) Patent No.: US 10,521,552 B2
(45) Date of Patent: Dec. 31, 2019

(54) METHOD AND COMPUTING DEVICE FOR IMPLEMENTING MULTIPLE MATCHING STRATEGIES

(71) Applicant: Change Healthcare Holdings, LLC, Nashville, TN (US)

(72) Inventors: Arien Malec, Oakland, CA (US); Chris Patterson, Oakland, CA (US)

(73) Assignee: CHANGE HEALTHCARE HOLDINGS, LLC, Nashville, TN (US)

( * ) Notice: Subject to any disclaimer, the term of this patent is extended or adjusted under 35 U.S.C. 154(b) by 945 days.

(21) Appl. No.: 15/086,379

(22) Filed: Mar. 31, 2016

(65) Prior Publication Data

US 2017/0286599 A1 Oct. 5, 2017

(51) Int. Cl.
*G06F 19/00* (2018.01)
*G06F 17/30* (2006.01)

(52) U.S. Cl.
CPC .................................. *G06F 19/00* (2013.01)

(58) Field of Classification Search
CPC ........ G16H 10/60; G16H 40/20; G16H 50/20; G16H 50/50; G16H 40/63; G16H 50/70; G16H 20/10; G06Q 50/24
See application file for complete search history.

(56) References Cited

U.S. PATENT DOCUMENTS

2015/0193583 A1* 7/2015 McNair ................. G16H 50/20
705/2

OTHER PUBLICATIONS

U.S. Appl. No. 14/450,883, filed Aug. 4, 2014, In re: Malec et al. entitled *Method and Apparatus for Defining a Level of Assurance in a Link Between Patient Records*.

* cited by examiner

*Primary Examiner* — Maroun P Kanaan
(74) *Attorney, Agent, or Firm* — Alston & Bird LLP

(57) ABSTRACT

A method, computer system and computer program product are provided to associate a record of a person and pre-existing records utilizing multiple matching strategies. The implementation of a plurality of matching strategies includes identifying link(s) between the record of the person and pre-existing records based upon an analysis pursuant to the respective matching strategy of demographic attributes of the person and respective individuals associated with the pre-existing records. The implementation of the plurality of matching strategies also includes associating the record of the person and a set of pre-existing records based upon the respective matching strategy. A relationship is then defined between the person and respective individuals associated with one or more sets of pre-existing records as defined by at least one of the plurality of matching strategies.

20 Claims, 4 Drawing Sheets

|  | Patient Matching Strategies | Flag 1 | Flag 2 | Flag 3 |
|---|---|---|---|---|
| Patient Record for Person |  |  |  |  |
| Patient Record 1 |  | ✓ |  |  |
| Patient Record 2 |  | ✓ | ✓ | ✓ |
| Patient Record 3 |  | ✓ |  | ✓ |
| Patient Record 4 |  |  | ✓ |  |
| Patient Record 5 |  | ✓ | ✓ |  |
| Link with PR 1 | 1 |  |  |  |
| Link with PR 2 | 1, 2, 3 |  |  |  |
| Link with PR 3 | 1, 3 |  |  |  |
| Link with PR 4 | 2 |  |  |  |
| Link with PR 5 | 1, 2 |  |  |  |

Figure 4

METHOD AND COMPUTING DEVICE FOR IMPLEMENTING MULTIPLE MATCHING STRATEGIES

TECHNOLOGICAL FIELD

An example embodiment of the present invention relates generally to the association of a first record with pre-existing records and, more particularly, to the association of records based upon the use of two or more matching strategies.

BACKGROUND

A variety of different types of records are being increasingly maintained in an electronic format so as to facilitate the identification, retrieval and sharing of the records while correspondingly reducing the need for physical records. One type of record that is being increasingly stored in electronic form is a patient record. A patient record may be maintained by a healthcare facility and may include information regarding a patient, such as various demographic attributes of the patient, e.g., name, address, date of birth, etc., and encounters of the patient with the healthcare facility. A patient record may also include or be associated with other information, such as one or more documents related to the patient's healthcare including, for example, the physician's notes, lab results and/or images of the patient, e.g., x-rays, magnetic resonance imaging (MRI) images, computer aided tomography (CAT) scans, etc.

Some persons may visit multiple healthcare facilities over the course of time. These healthcare facilities may be owned and operated by different healthcare organizations. Each healthcare facility may maintain a patient record, but the patient records maintained by the different healthcare facilities may be independent of one another since the different healthcare organizations that own and operate the healthcare facilities may not share patient records or otherwise cooperate to maintain a common patient record.

In order to have a more complete and comprehensive understanding of a patient's health, a physician or other healthcare practitioner may wish to have access to all of the patient records, regardless of the healthcare facility that created and maintains the patient records. However, in an instance in which a person has visited multiple healthcare facilities that are owned or operated by different healthcare organizations and unless the person has collected and provides a physician or other healthcare practitioner with all of their patient records from the various healthcare facilities that they have visited, the physician or other healthcare practitioner may have difficulty accessing or be unable to access the plurality of patient records maintained for the person by the various healthcare facilities. This difficulty may be exacerbated by the assignment of a different, unique patient identifier to the patient by at least some of the healthcare facilities since a healthcare practitioner may be unaware of the patient identifier associated with the patient by other healthcare facilities and, as such, may have difficulty identifying the patient to the other healthcare facilities.

Health Information Exchanges (HIEs) have been developed in order to, among other things, process patient records including matching patient records that are determined to be associated with the same person. For example, health information exchanges are configured to identify and link those patient records that are associated with the same person even though the patient records may have been created by different healthcare organizations and may have different patient identifiers associated therewith. By linking the patient records from various healthcare organizations that are associated with the same person, a healthcare professional may have a more complete picture of the patient's medical history.

A variety of patient matching strategies have been developed in order to link patient records that are associated with the same person. For example, the various patient matching strategies may rely upon different demographic information drawn from the patient records in an effort to determine whether the patient records are associated with the same person. Additionally or alternatively, the various patient matching strategies may differently weight matches between different types of demographic information extracted from the patient records and/or may the patient records to satisfy different thresholds in order to determine whether two or more patient records are associated with the same person.

Based upon their design, some patient matching strategies are more aggressive in that a greater percentage of patient records are identified to be associated with the same person, while other patient matching strategies are more conservative in that a lower percentage of patient records are identified to be associated with the same person. While each patient matching strategy facilitates the identification of patient records that are associated with the same person, each patient matching strategy is generally designed in such a manner as to have both strengths and weaknesses in regards to the identification of patient records associated with the same person. For example, more aggressive patient matching strategies may suffer from an increased percentage of false positives in which patient records are incorrectly identified to be associated with this same person, while more conservative patient matching strategies may suffer from an increased percentage of false negatives in which a larger percentage of patient records that are actually associated with the person in question are not identified as being so associated. As a result, different healthcare organizations and/or different health information exchanges may employ different patient matching strategies dependent upon the tolerance of the respective organization or exchange to false positives and/or false negatives. As noted above, however, implementation of each patient matching strategy results in at least some undesirable uncertainty in the accuracy of the results.

BRIEF SUMMARY

A method, computer system and computer program product are provided in accordance with an example embodiment in order to associate a record with one or more pre-existing records utilizing multiple matching strategies. These records may, for example, each be associated with the same person. By utilizing a plurality of matching strategies, the method, computer system and computer program product of an example embodiment may identify records associated with the same person in a more accurate manner. In this regard, the method, computer system and computer program product of an example embodiment may improve the accuracy of the records that are identified to be associated with a particular person, both in terms of the reduction of false positives and the reduction of false negatives. Thus, the method, computer system and computer program product of an example embodiment may rely upon the advantageous aspects of the plurality of matching strategies, while negating at least some of the negative aspects of the plurality of matching strategies.

In accordance with one embodiment, a method is provided that includes implementing a plurality of different matching strategies to separately associate a record associated with a person and pre-existing records. In this regard, the implementation of the plurality of different matching strategies includes implementing a first matching strategy to associate a record associated with a person and pre-existing records. The implementation of the first matching strategy includes identifying, with processing circuitry, one or more links between the record associated with the person and pre-existing records. The identification of one or more links includes identifying one or more links based upon an analysis pursuant to the first matching strategy of demographic attributes of the person and respective individuals associated with the pre-existing records. The implementation of the first matching strategy also includes associating the record associated with the person and a first set of pre-existing records based upon the first matching strategy including the one or more links identified thereby. The implementation of the plurality of different matching strategies also includes implementing a second matching strategy, different than the first matching strategy, to associate the record associated with the person and pre-existing records. The implementation of the second matching strategy includes identifying, with the processing circuitry, one or more links between the record associated with the person and pre-existing records. The identification of one or more links includes identifying one or more links based upon an analysis pursuant to the second matching strategy of demographic attributes of the person and the respective individuals associated with the pre-existing records. The implementation of the second matching strategy also includes associating the record associated with the person and a second set of pre-existing records, different than the first set of pre-existing records, based upon the second matching strategy including the one or more links identified thereby. In this example embodiment, the method further includes defining a relationship between the person and respective individuals associated with at least one of the first set or the second set of pre-existing records as defined by at least one of the first or second matching strategies.

The implementation of the first and second matching strategies may include identifying one or more links between the record associated with the person and pre-existing records utilizing a first match threshold in conjunction with the analysis pursuant to the first matching strategy and a second match threshold, different than the first match threshold, in conjunction with the analysis pursuant to the second matching strategy. In an example embodiment, the implementation of the first and second matching strategies includes identifying one or more links between the record associated with the person and pre-existing records with demographic attributes that are found to satisfy a match threshold being differently weighted pursuant to the first matching strategy than pursuant to the second matching strategy. The plurality of matching strategies including the first and second matching strategies may be concurrently implemented.

The method of an example embodiment may also include identifying each link between the record associated with the person and pre-existing records that is identified by one or more of the plurality of matching strategies based upon the respective matching strategy via which the link was identified. The method of an example embodiment may also include defining a confidence level associated with the relationship between the person and respective individuals associated with at least one of the first set or the second set of pre-existing records. The confidence level is dependent upon whether the respective individuals are associated with only one of the first set or the second set of pre-existing records or are associated with both of the first set and the second set of pre-existing records. In an example embodiment, the method may also include receiving a selection of one of the first or second matching strategies or a modification of at least one of the first or second matching strategies based upon an evaluation of the first and second sets of pre-existing records as defined by the first and second matching strategies, respectively.

In another example embodiment, a computer system is provided that includes a processing circuitry configured to implement a plurality of different matching strategies to separately associate a record associated with a person and pre-existing records. The implementation of the plurality of different matching strategies includes implementing a first matching strategy to associate a record associated with a person and pre-existing records. In this regard, the processing circuitry is configured to implement the first matching strategy by identifying one or more links between the record associated with the person and pre-existing records. The identification of one or more links includes identifying one or more links based upon an analysis pursuant to the first matching strategy of demographic attributes of the person and respective individuals associated with the pre-existing records. The processing circuitry is also configured to implement the first matching strategy by associating the record associated with the person and a first set of pre-existing records based upon the first matching strategy including the one or more links identified thereby. The implementation of the plurality of different matching strategies also includes implementing a second matching strategy, different than the first matching strategy, to associate the record associated with the person and pre-existing records. The processing circuitry is configured to implement the second matching strategy by identifying one or more links between the record associated with the person and pre-existing records. The identification of one or more links includes identifying one or more links based upon an analysis pursuant to the second matching strategy of demographic attributes of the person and the respective individuals associated with the pre-existing records. The processing circuitry is also configured to implement the second matching strategy by associating the record associated with the person and a second set of pre-existing records, different than the first set of pre-existing records, based upon the second matching strategy including the one or more links identified thereby. The processing circuitry is further configured to define a relationship between the person and respective individuals associated with at least one of the first set or the second set of pre-existing records as defined by at least one of the first or second matching strategies.

The processing circuitry of an example embodiment is configured to implement the first and second matching strategies by identifying one or more links between the record associated with the person and pre-existing records utilizing a first match threshold in conjunction with the analysis pursuant to the first matching strategy and a second match threshold, different than the first match threshold, in conjunction with the analysis pursuant to the second matching strategy. In an example embodiment, the processing circuitry is configured to implement the first and second matching strategies by identifying one or more links between the record associated with the person and pre-existing records with demographic attributes that are found to satisfy a match threshold being differently weighted pursuant to the first matching strategy than pursuant to the second matching strategy. The processing circuitry of an example embodiment is configured to implement the plurality of different matching strategies by concurrently implementing the plurality of matching strategies.

In an example embodiment, the processing circuitry is further configured to identify each link between the record associated with the person and pre-existing records that is identified by one or more of the plurality of matching strategies based upon the respective matching strategy via which the link was identified. The processing circuitry of an example embodiment is further configured to define a confidence level associated with the relationship between the person and respective individuals associated with at least one of the first set or the second set of pre-existing records. The confidence level is dependent upon whether the respective individuals are associated with only one of the first set or the second set of pre-existing records or are associated with both of the first set and the second set of pre-existing records. In an example embodiment, the processing circuitry is further configured receive a selection of one of the first or second matching strategies or a modification of at least one of the first or second matching strategies based upon an evaluation of the first and second sets of pre-existing records as defined by the first and second matching strategies, respectively.

In a further example embodiment, a computer program product is provided that includes a non-transitory computer readable storage medium having program code portions stored thereon with the program code portions configured, upon execution, to implement a plurality of different matching strategies to separately associate a record associated with a person and pre-existing records. The implementation of the plurality of different matching strategies includes implementing a first matching strategy to associate a record associated with a person and pre-existing records. In this regard, the program code portions are configured to implement the first matching strategy by identifying one or more links between the record associated with the person and pre-existing records. The identification of one or more links includes identifying one or more links based upon an analysis pursuant to the first matching strategy of demographic attributes of the person and respective individuals associated with the pre-existing records. The program code portions are also configured to implement the first matching strategy by associating the record associated with the person and a first set of pre-existing records based upon the first matching strategy including the one or more links identified thereby. The implementation of the plurality of different matching strategies also includes implementing a second matching strategy, different than the first matching strategy, to associate the record associated with the person and pre-existing records. The program code portions are configured to implement the second matching strategy by identifying one or more links between the record associated with the person and pre-existing records. The identification of one or more links includes identifying one or more links based upon an analysis pursuant to the second matching strategy of demographic attributes of the person and the respective individuals associated with the pre-existing records. The program code portions are also configured to implement the second matching strategy by associating the record associated with the person and a second set of pre-existing records, different than the first set of pre-existing records, based upon the second matching strategy including the one or more links identified thereby. The program code portions are further configured to define a relationship between the person and respective individuals associated with at least one of the first set or the second set of pre-existing records as defined by at least one of the first or second matching strategies.

The program code portions of an example embodiment are configured to implement the first and second matching strategies by identifying one or more links between the record associated with the person and pre-existing records utilizing a first match threshold in conjunction with the analysis pursuant to the first matching strategy and a second match threshold, different than the first match threshold, in conjunction with the analysis pursuant to the second matching strategy. In an example embodiment, the program code portions are configured to implement the first and second matching strategies by identifying one or more links between the record associated with the person and pre-existing records with demographic attributes that are found to satisfy a match threshold being differently weighted pursuant to the first matching strategy than pursuant to the second matching strategy. The program code portions of an example embodiment are configured to concurrently implement the plurality of matching strategies.

The program code portions of an example embodiment are further configured to identify each link between the record associated with the person and pre-existing records that is identified by one or more of the matching strategies based upon the respective matching strategy via which the link was identified. In an example embodiment, the program code portions are further configured to define a confidence level associated with the relationship between the person and respective individuals associated with at least one of the first set or the second set of pre-existing records. The confidence level is dependent upon whether the respective individuals are associated with only one of the first set or the second set of pre-existing records or are associated with both of the first set and the second set of pre-existing records.

BRIEF DESCRIPTION OF THE DRAWINGS

Figure 1:
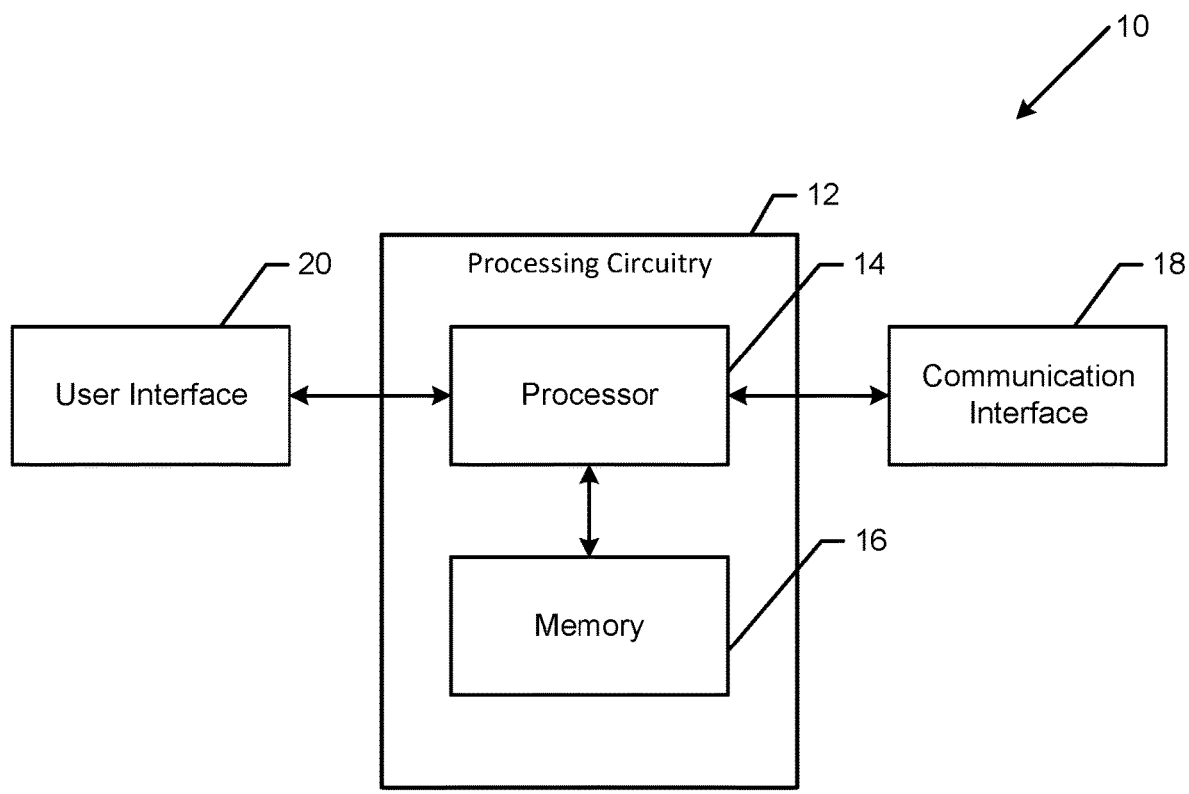
Figure 2:
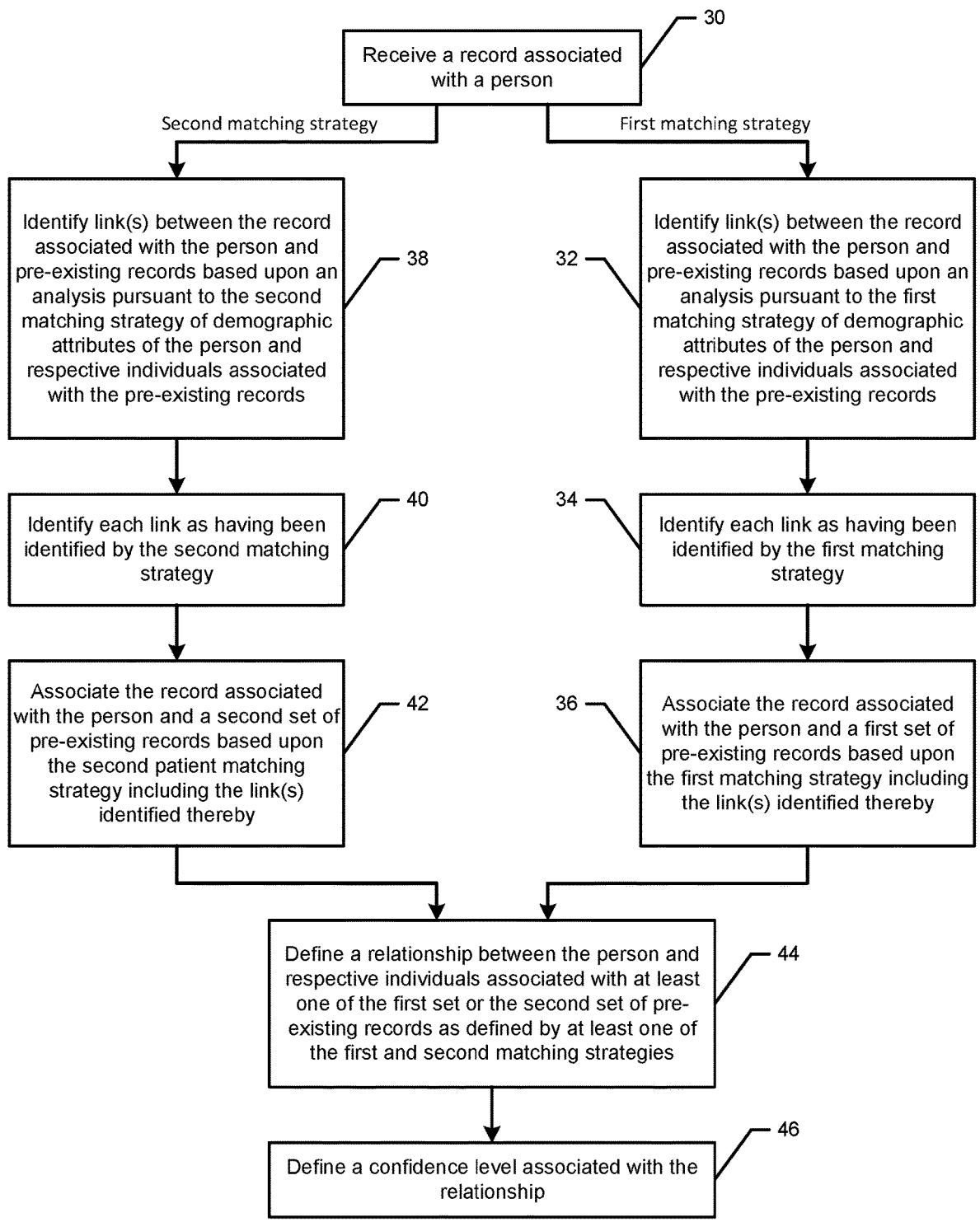
Figure 3:
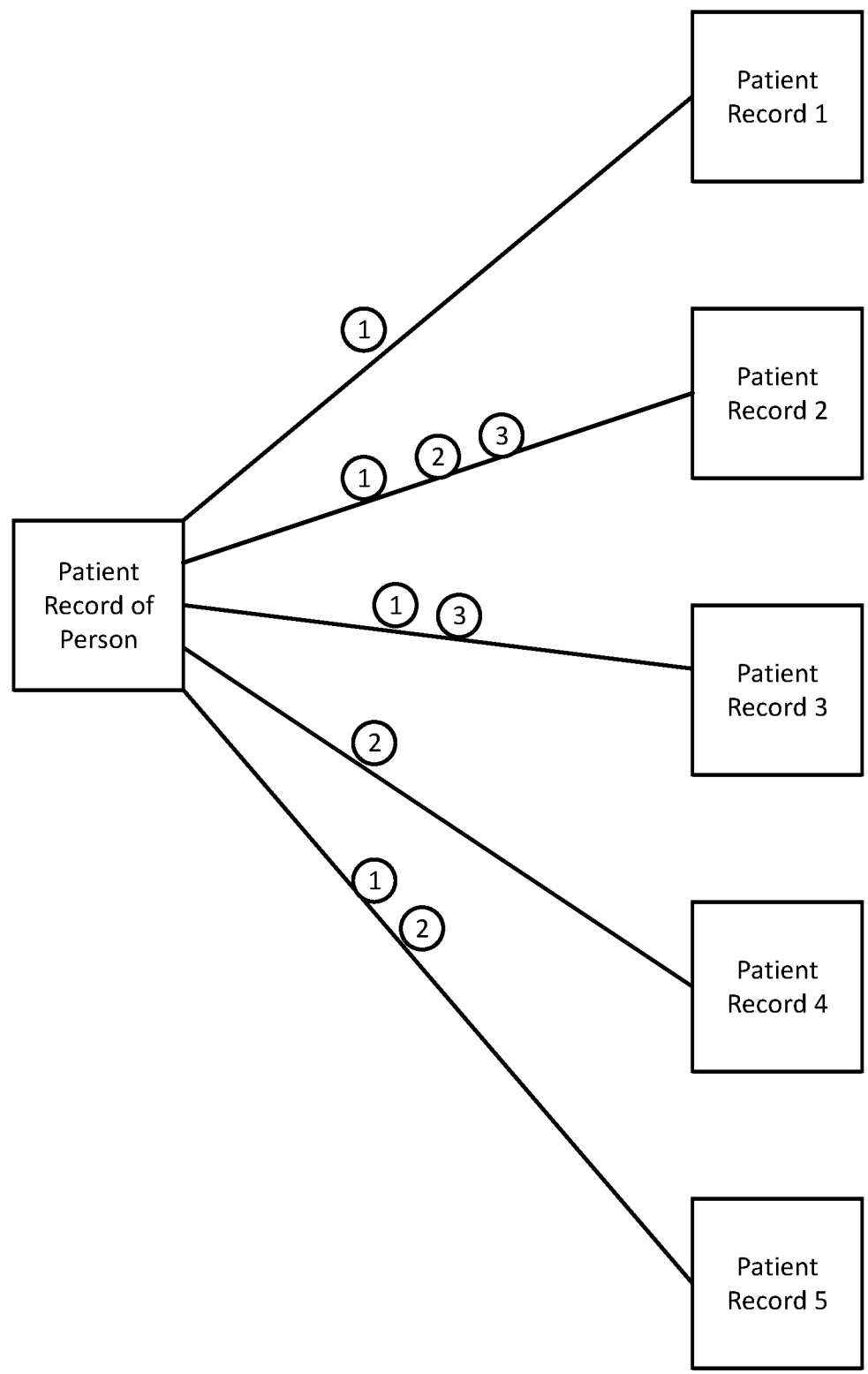

Having thus described certain example embodiments of the invention in general terms, reference will now be made to the accompanying drawings, which are not necessarily drawn to scale, and wherein:

FIG. 1 is a block diagram of a computer system that may be specifically configured in accordance with an example embodiment of the present invention;

FIG. 2 is a flow chart illustrating operations performed, such as by the computer system of FIG. 1, in conjunction with the implementation of multiple patient matching strategies in accordance with an example embodiment of the present invention;

FIG. 3 is a representation of links established between the patient record of a person and a plurality of other pre-existing patient records; and FIG. 4 is a table constructed in accordance with the links established as shown in FIG. 3.

DETAILED DESCRIPTION

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Further, the apparatus and method of example embodiments of the present invention will be primarily described in conjunction with medical-imaging applications.

It should be understood, however, that the apparatus and method may be utilized in conjunction with a variety of other applications, both in the medical industry and outside the medical industry. Like numbers refer to like elements throughout.

A method, computer system and computer program product are provided in accordance with an example embodiment in order to utilize a plurality of matching strategies to identify records, such as patient records generated by a plurality of different healthcare organizations, that are associated with the same person. The concurrent implementation of a plurality of different matching strategies increases the accuracy of the results, both in terms of a reduction of false positives and a reduction in false negatives, relative to the individual implementation of any of the matching strategies. Thus, in the example of identifying matching patient records, a healthcare professional may obtain a more accurate and complete picture of a patient's medical history and may be able to have greater confidence in the patient records that are identified to be associated with the same person by the concurrent implementation of a plurality of different matching strategies.

The records that are analyzed pursuant to the various matching strategies may be any of a wide variety of records. For purposes of illustration, but not of limitation, the method, computer system and computer program product will now be described in the context of patient records that are analyzed pursuant to various patient matching strategies. Each patient record may include a plurality of demographic attributes associated with the patient, such as the first, middle and last name of the person, the mailing address of the person, the date of birth of the person, etc. Additionally, a patient record may include information describing one or more encounters of a patient with a respective healthcare facility. Patient records may include information regarding a wide variety of encounters including office visits, laboratory tests, hospital admittances, imaging appointments, etc. Some patient records may also include or otherwise be associated with one or more documents. The documents may be associated with one or more of the encounters for which the patient record includes information. The documents may include, for example, laboratory results, notes taken by a physician during an office visit, imaging studies or the like.

Patient records also generally include one or more pieces of healthcare data. At least some of the healthcare data may need to be transformed prior to being further processed. For example, blood pressure may be provided by different types of devices and may need to be transformed to have a normalized value. Other transformations may include the parsing of healthcare data into its constituent data elements, or the performance of secondary calculations to determine the numerator or a denominator code for a clinical quality measure. In order to automatically trigger any necessary transformations, a declarative type conversion may be optionally associated with data types that require transformation. Upon receipt of healthcare data of a type having a declarative type conversion associated therewith, the healthcare data may be automatically transformed. The patient record may, in turn, store the original healthcare data and the results of the transformation.

One example of a transformation is a terminology conversion, such as from National Drug Code (NDC) terminology values in which the data is received to RxNorm terminology values in which the data will be processed downstream. In an example embodiment, both primitive and FHIR-based ontology topics are maintained by the computer system 10. At each level, values may be stored in triplets, e.g., code system, code, original value (and possibly other values regarding the coding system that was used). Graph queries to ontology objects or core topics may specify a target coding system, e.g., As RxNorm, and, in response, the graph engine, such as embodied by the processing circuitry 12, may traverse the terminology graph to enable conversion to the specified terminology. The graph engine therefore includes a formally specified graph and the ontology query language containing keywords specifying terminology casting, that is, an implementation of the query language containing keywords specifying terminology casting. Thus, this example transformation is configured to implement automated propagation of the terminology query.

The patient records may be created by the healthcare facility that treats the patient. The healthcare facilities may include any of a variety of facilities visited by a patient that may create and maintain patient records including hospitals, physician practices, laboratories, imaging facilities or the like. In instances in which the patient has visited a plurality of different healthcare facilities, the patient may have patient records that have been created by each of a plurality of different healthcare providers. Each healthcare facility may store the patient records for the patients that have been treated by the respective healthcare facility in order to memorialize the health care proved to the patient by the respective healthcare facility. As such, the patient records created by a plurality of healthcare facilities for respective patients are not generally stored in a common database, but are, instead, stored in a distributed fashion amongst the plurality of healthcare providers.

Although each healthcare facility may assign a patient identifier for each patient treated by the respective healthcare facility that is unique within the healthcare facility, a patient is not generally assigned a universal patient identifier that uniquely identifies the patient relative to each of the healthcare facilities. In order to facilitate the identification of patient records that are associated with patients who are considered to match a person in question, information regarding the patient records, such as the information regarding the demographic attributes associated with the patient, may be provided by the healthcare facilities to a computer system that may be configured to utilize a plurality of patient matching strategies to identify links between a patient record associated with a person and pre-existing patient records that may be associated with the same person.

The computer system of an example embodiment is configured to receive patient records from the healthcare facilities and to identify links between a patient record associated with a person and pre-existing patient records associated with respective patients (regardless of the healthcare facility that provided the patient records) who are considered to match a person in question, such as a person seeking admittance by one of the healthcare facilities. The computer system may be associated with the Health Information Exchange (HIE) or other data platform and, as such, may be embodied by one or more servers, computer workstations, desktop or laptop computers or the like in accordance with one example embodiment. However, the computer system may be embodied in various other manners, such as by a payor or other healthcare organization. Regardless of the manner in which the computer system is embodied, the computer system 10 of an example embodiment may be configured as shown FIG. 1. In this example embodiment, the computer system includes or is otherwise be in communication with processing circuitry 12 that is configurable to perform actions in accordance with one or more example embodiments disclosed herein. In this regard, the processing circuitry may be configured to perform and/or control performance of one or more functionalities of the computer system in accordance with various example embodiments, and thus may provide means for performing functionalities of the computer system. The processing circuitry may be configured to perform data processing, application execution and/or other processing and management services according to one or more example embodiments.

In some example embodiments, the processing circuitry 12 may include a processor 14 and, in some embodiments, such as that illustrated in FIG. 1, may further include memory 16. The processing circuitry may be in communication with or otherwise control a communication interface 18 and, in some embodiments, a user interface 20. As such, the processing circuitry may be embodied as a circuit chip (e.g., an integrated circuit chip) configured (e.g., with hardware, software or a combination of hardware and software) to perform operations described herein.

The processor 14 may be embodied in a number of different ways. For example, the processor may be embodied as various processing means such as one or more of a microprocessor or other processing element, a coprocessor, a controller or various other computing or processing devices including integrated circuits such as, for example, an ASIC (application specific integrated circuit), an FPGA (field programmable gate array), or the like. Although illustrated as a single processor, it will be appreciated that the processor may comprise a plurality of processors. The plurality of processors may be in operative communication with each other and may be collectively configured to perform one or more functionalities of the computer system 10 as described herein. The plurality of processors may be embodied on a single computing device or distributed across a plurality of computing devices collectively configured to function as the computer system. In some example embodiments, the processor may be configured to execute instructions stored in the memory 16 or otherwise accessible to the processor. As such, whether configured by hardware or by a combination of hardware and software, the processor may represent an entity (e.g., physically embodied in circuitry—in the form of processing circuitry 12) capable of performing operations according to embodiments of the present invention while configured accordingly. Thus, for example, when the processor is embodied as an ASIC, FPGA or the like, the processor may be specifically configured hardware for conducting the operations described herein. Alternatively, as another example, when the processor is embodied as an executor of software instructions, the instructions may specifically configure the processor to perform one or more operations described herein.

In some example embodiments, the memory 16 may include one or more non-transitory memory devices such as, for example, volatile and/or non-volatile memory that may be either fixed or removable. In this regard, the memory may comprise a non-transitory computer-readable storage medium. It will be appreciated that while the memory is illustrated as a single memory, the memory may comprise a plurality of memories. The plurality of memories may be embodied on a single computing device or may be distributed across a plurality of computing devices collectively configured to function as the computer system 10. The memory may be configured to store information, data, applications, instructions and/or the like for enabling the computer system to carry out various functions in accordance with one or more example embodiments. For example, the memory may be configured to buffer input data for processing by the processor 12. Additionally or alternatively, the memory may be configured to store instructions for execution by the processor. As yet another alternative, the memory may include one or more databases that may store a variety of files, contents or data sets, such as the pre-existing patient records discussed below. Among the contents of the memory, applications may be stored for execution by the processor in order to carry out the functionality associated with each respective application. In some cases, the memory may be in communication with one or more of the processor, user interface, or communication interface 18 via a bus or buses for passing information among components of the computer system.

The user interface 20 may be in communication with the processing circuitry 12 to receive an indication of a user input at the user interface and/or to provide an audible, visual, mechanical or other output to the user. As such, the user interface may include, for example, a keyboard, a mouse, a joystick, a display, a touch screen display, a microphone, a speaker, a Light Emitting Diode (LED), a lighting device, an electronic sensor for capturing human body movements, and/or other input/output mechanisms. In embodiments in which the computer system 10 is implemented on a server, aspects of the user interface may be limited, or the user interface may even be eliminated. For example, the computer system may act as a server or host device, with a user interface provided by a client application.

The communication interface 18 may include one or more interface mechanisms for enabling communication with other devices and/or networks, such as with the healthcare facilities. In this regard, communication with the healthcare facilities includes communication with one or more computing devices of the respective healthcare facilities. In some cases, the communication interface may be any means such as a device or circuitry embodied in either hardware, or a combination of hardware and software that is configured to receive and/or transmit data from/to a network and/or any other device or module in communication with the processing circuitry 12. By way of example, the communication interface may be configured to enable the computer system 10 to communicate with the healthcare facilities via a wireless network, such as a wireless local area network (WLAN), cellular network, and/or the like. Additionally or alternatively, the communication interface may be configured to enable the computer system to communicate with the healthcare facilities via a wireline network. In some example embodiments, the communication interface may be configured to enable communication between the computer system and one or more healthcare facilities via the internet. Accordingly, the communication interface may, for example, include an antenna (or multiple antennas) and supporting hardware and/or software for enabling communications with a wireless communication network (e.g., a wireless local area network, cellular network, and/or the like) and/or a communication modem or other hardware/software for supporting communication via cable, digital subscriber line (DSL), universal serial bus (USB), Ethernet or other methods.

Having now described computer system 10 configured to implement and/or support implementation of various example embodiments, features of several example embodiments will now be described. It will be appreciated that the following features are non-limiting examples of features provided by some example embodiments. Further, it will be appreciated that embodiments are contemplated within the scope of disclosure that implement various subsets or combinations of the features further described herein. Accordingly, it will be appreciated that some example embodiments may omit one or more of the following features and/or implement variations of one or more of the following features.

In an example embodiment, the method, computer system 10 and computer program product are event-driven with the patient matching operations being initiated in response to the receipt of a patient record associated with a person. As such, the computer system may include means, such as the communication interface 18, the processing circuitry 12, the processor 14 or the like, for receiving a patient record associated with person. See block 30 of FIG. 2. In an example embodiment in which the computer system is embodied by health information exchange, the patient record associated with the person may be received from any of the healthcare organizations associated with and in communication with the health information exchange. In an example embodiment, the patient record associated with the person that has been created and submitted by a healthcare organization may have a high degree of certainty that the patient record is associated with the person as a result of, for example, confirmation by the healthcare organization that the person is, in fact, the actual patient, such as by reference to the patient's driver's license. The computer system is configured to receive the patient record associated with the person in various manners, such as via wireless communications, wireline communication or the like via the communication interface. In an example embodiment, the computer system is in communication with a plurality of healthcare facilities and is configured to receive the patient record associated with the person from a respective healthcare facility via an application programming interface (API) or via a portal application, e.g., a web browser interface. The patient record associated with the person may be stored, for example, by memory 16 of the computer system.

In response to receipt of the patient record associated with the person, pre-existing patient records that are also associated with the person may be identified and linked to the patient record that was received. As such, the computer system 10 includes means, such as the processing circuitry 12, the processor 14 or the like, for implementing a plurality of different patient matching strategies. By way of illustration, the implementation of two different patient matching strategies will be described, although any number of additional patient matching strategies may also be concurrently implemented in other embodiments. In an example embodiment, the plurality of patient matching strategies are implemented concurrently and in parallel with one another, although the patient matching strategies may be implemented in a sequential fashion on other embodiments.

The implementation of each patient matching strategy is configured to separately identify one or more links between the patient record associated with the person and one or more pre-existing patient records based upon an analysis pursuant to the respective patient matching strategy. The pre-existing patient records may be stored, for example, by memory 16 or by a database maintained by or otherwise accessible by the computer system 10. The computer system therefore includes means, such as the processing circuitry 12, the processor 14 or the like, for implementing the plurality of different patient matching strategies in order to separately identify one or more links between the patient record associated with the person and pre-existing patient records based upon an analysis pursuant to the respective patient matching strategy. In this regard, the computer system includes means, such as the processing circuitry, the processor or the like, for implementing the first patient matching strategies in order to identify one or more links between the patient record associated with the person and pre-existing patient records based upon an analysis pursuant to the first patient matching strategy. See block 32 of FIG. 2. The analysis conducted pursuant to the first patient matching strategy may compare demographic attributes of the person, such as identified by the patient record associated with the person, and demographic attributes of respective patients associated with the pre-existing patient records. While various types of demographic attributes may be utilized, examples include first name, last name, date of birth, gender and zipcode. Other examples may include information extracted from a patient's driver license including height, weight, hair color and/or eye color which may be compared to similar information included in the patient records. Still further examples include the identifier associated with the health device, such as a pacemaker or other device implanted within the patient. In this regard, the health device may include a unique identifier that, in turn, is registered with the patient.

This analysis is defined by the first patient matching strategy by an identification of the particular demographic attributes to be compared and/or the weights to be associated with each different type of demographic attribute that is found to be matching between the person and the respective patients associated with the pre-existing patient records. The first patient matching strategy may also identify the threshold at which the patient record associated with the person is configured to match a pre-existing patient record. For example, the sum of the weights associated with the demographic attributes that are determined to match between the person and the patient associated with a respective pre-existing patient record may be compared to the threshold with the patient associated with the respective pre-existing patient record being considered to match the person in an instance in which the threshold is satisfied. Based upon the demographic attributes that are to be considered during the matching process as well as the weight associated with each of the matching demographic attributes and the threshold that is utilized in order to distinguish between patient records that match and patient records that do not match, the first patient matching strategy may be tailored to be appropriately conservative or aggressive or have some intermediate level of risk associated therewith.

For those pre-existing patient records that are identified to be associated with the person, a link between the pre-existing patient records and the patient record that was received may be established. The computer system 10 includes means, such as the processing circuitry 12, the processor 14 or the like, for identifying the link as having been established or otherwise identified by the first patient matching strategy, such as by associating an indication with the respective link with the indication identifying the particular patient matching strategy that established the link. See block 34 of FIG. 2. By way of example, the processing circuitry may be configured to define a table or other structure in memory 16 that identifies the plurality of patient records including those patient records that are received and the pre-existing patient records and that also identifies the links between the patient records by including, for example, an indication of the respective patient matching strategy that identified the respective link. The patient records may also continue to be separately maintained, such as in memory 16 or another database, and are not converged or otherwise physically combined following the identification of links between patient records, thereby permitting the patient records to be reviewed in conjunction with the implementation of multiple patient matching strategies.

The computer system 10 also includes means, such as the processing circuitry 12, the processor 14 or the like, for associating the patient record associated with the person that was received and a first set of pre-existing patient records based upon the first patient matching strategy including the links identified thereby. See block 36 of FIG. 2. In this regard, the processing circuitry is configured to identify those pre-existing patient records for which links were established with the patient record associated with the person pursuant to the first patient matching strategy as the first set of matching patient records. As described above, the processing circuitry of this example embodiment may also modify the table or other memory structure to identify the first set of patient records that have been associated with the patient record associated with the person pursuant to the first patient matching strategy, such as by including a flag with each patient record of the first set that has been identified by the first patient matching strategy.

Typically concurrent with the implementation of the first patient matching strategy, the computer system 10 also includes means, such as the processing circuitry 12, the processor 14 or the like for implementing a second patient matching strategy. See block 38 of FIG. 2. The second patient matching strategy is also configured to identify pre-existing patient records that are associated with the same person with which the patient record that was received is associated. However, the second patient matching strategy is differently configured than the first patient matching strategy such that implementation of the second patient matching strategy may identify a different set of pre-existing patient records as being associated with the patient record that was received and is associated with the person. The second patient matching strategy may differ from the first patient matching strategy in various manners including configuration of the second patient matching strategy to consider different demographic attributes of the patient record in conjunction with the matching process, the application of different weights to different types of matching attributes and/or the use of a different threshold in conjunction with the identification of patient records that are associated with the same person. As such, the second patient matching strategy may be differently tailored than the first patient matching strategy. For example, one of the patient matching strategies may be more aggressive, while the other patient matching strategy is more conservative.

In conjunction with the implementation of the second patient matching strategy, the processing circuitry 12 is configured to identify one or more links between the patient record associated with the person and pre-existing patient records based upon an analysis pursuant to the second patient matching strategy including an analysis of demographic attributes of the person and demographic attributes of the respective patients associated with pre-existing patient records. Based upon that analysis, the computer system 10 includes means, such as the processing circuitry 12, the processor 14, the memory 16 or the like, for identifying each link between the patient record associated with the person and the pre-existing patient records that were identified as being associated with the same person pursuant to the second patient matching strategy. See block 40 of FIG. 2. Further, the computer system of an example embodiment includes means, such as the processing circuitry, the processor, the memory or the like, for associating the patient record associated with the person and a second set of pre-existing patient records. See block 42. The second set of pre-existing patient records may be those pre-existing patient records for which a link has been identified with the patient record associated with the person based upon the second patient matching strategy including the one or more links identified thereby.

As described above, the processing circuitry 12 may be configured to implement the second patient matching strategy by defining a table or other memory structure that identifies the patient records and the links that are identified therebetween. The table or other memory structure may also be constructed to provide an indication that the links were established by the second patient matching strategy and those patient records having links that were identified pursuant to the second patient matching strategy may be correspondingly flagged.

As noted above, various patient matching strategies may be implemented. For example, a patient matching strategy that relies upon the level of link assurance may be implemented as one of the patient matching strategies. In this regard, a patient matching strategy that relies upon the level of link assurance is described by U.S. patent application Ser. No. 14/450,883 entitled Method and Apparatus for Defining a Level of Assurance in a Link Between Patient Records and filed on Aug. 4, 2014, the entire contents of which are incorporated herein by reference. Other patient matching strategies may be specific to and designed by a respective healthcare organization and may be particularly tailored to the risk tolerance of the respective healthcare organization in relation to the accuracy, both in terms of completeness and integrity, of the patient records that are identified to be associated with the same person.

As also described above, the computer system 10 may be configured to implement more than two patient matching strategies, such as three or more patient matching strategies, with each patient matching strategy configured in a different manner. As a result of the different configurations of the various patient matching strategies, the respective sets of pre-existing patient records that are identified by the different patient matching strategies may be different with some patient records being identified as being associated with the person by one patient matching strategy, but not another. By way of example, FIG. 3 depicts an example in which a patient record of a person that is received is analyzed pursuant to first, second and third patient matching strategies relative to a plurality of pre-existing patient records. As shown in FIG. 3, five different pre-existing patient records, designated patient record 1, patient record 2, . . . patient record 5, were identified by one or more of the first, second and third patient matching strategies as being associated with the patient record associated with the person that was received. In this depiction, links are established between the patient record of the person that was received and the respective pre-existing patient records and an indication is provided in conjunction with the link of the one or more patient matching strategies that created the link therebetween. In this regard, the links established by the first patient matching strategy are identified by an encircled 1, the links established by the second patient matching strategy is identified by an encircled 2 and the links established by a third patient matching strategy are identified by an encircled 3.

As shown in this example, the first patient matching strategy is relatively aggressive and creates a first set of pre-existing patient records that are associated with the patient record of the person with the first set including patient record 1, patient record 2, patient record 3 and patient record 5. Additionally, the second patient matching strategy has an intermediate level of conservativeness and aggressiveness and identifies a second set of pre-existing patient records to be associated with the patient record associated with the person that was received with the second set including patient record 2, patient record 4 and patient record 5. The third patient matching strategy is even more conservative and identifies a third set of pre-existing patient records that are associated with the patient record associated with the person that was received with the third set including patient record 2 and patient record 3. Thus, FIG. 3 depicts different sets of pre-existing patient records being identified by the different patient matching strategies with the resulting sets dependent upon the configuration of the respective patient matching strategy.

By way of example of a table constructed by the processing circuitry 12 of an example embodiment, FIG. 4 depicts a table representative of the links established in accordance with FIG. 3. In this regard, the table identifies each of the patient records as well as the links therebetween. The table also includes an indication associated with each of the links as to each patient matching strategy that established the respective link. Further, the patient records that are included in each of the first, second and third sets generated by the first, second and third patient matching strategies, respectively, are flagged as described above.

In one embodiment, the computer system 10 is configured to receive user input following the identification of the links by the multiple patient matching strategies. The user input may tailor the results of the patient matching strategies by defining one or more additional links between the patient record associated with the person that was received and one or more pre-existing patient records. Additionally or alternatively, the user input may eliminate or remove one or more links that were established by at least one of the patient matching strategies. In an example embodiment, the computer system may employ machine learning to adapt one or more of the patient matching strategies based upon the link(s) that are added or removed by the user input.

The computer system 10 also includes means, such as the processing circuitry 12, the processor 14 or the like, for defining the relationship between the person (associated with the patient record that was received to trigger this process) and respective patients associated with the pre-existing patient records that are included in at least one of the first or second sets of pre-existing patient records as defined by the first or second patient matching strategies, respectively. See block 44 of FIG. 2. In this regard, the computer system, such as the processing circuitry, is configured to reconcile and cohere the output of the plurality of different matching strategies. For example, implementation of the first matching strategy may determine that Jon Snow, John Snow and Jonathan Snow are the same person and the second matching strategy may determine that Jon Snow, John Snow and Jon Snowe are the same person. As such, the processing circuitry of an example embodiment may be configured to reconcile the results of the first and second matching strategies to form a set of patient records for Jon Snow, John Snow, Jonathan Snow and Jon Snowe who are considered to match the person (associated with the patient record that was received to trigger this process).

The computer system 10, such as the processing circuitry 12, may be differently configured so as to identify generally more or generally fewer patient records depending upon the desired confidence level in the results. For example, the processing circuitry may be configured to only identify the person and the patients associated with pre-existing patient records to be the same in an instance in which the pre-existing patient records are included in each of the different sets of pre-existing patient records identified by the different patient matching strategies. Thus, in this example, a pre-existing patient record would have to be identified to be a match by each of the patient matching strategies and, as a result, be included in each of the different sets of pre-existing patient records in order for the patient with which the pre-existing patient record is associated to be considered as the same as the person with which the patient record that was received is associated. With reference to FIG. 3 by way of example, only the patient associated with patient record 2 would be considered the same as the person with which the patient record that was received in accordance with this approach. By requiring the pre-existing patient record to be identified by each of the plurality of patient matching strategies, the result would likely have a relatively high confidence level in the result being correct, but may have a greater percentage of false negatives by failing to identify one or more other pre-existing patient records that are also associated with the same person.

As another approach, the processing circuitry 12 may be configured to be more aggressive and, as such, may identify the patient associated with any pre-existing patient record that is included in any one or more of the different sets of pre-existing patient records created by the different patient matching strategies to be the same as the person with which the patient record that was received is associated. By way of example, each of patient records 1, 2, 3, 4 and 5 in the example depicted in FIG. 3 would be associated with the patient record of the person that was received since each of patient record 1, 2, 3, 4 and 5 were identified by one of the patient matching strategies. This more aggressive approach will provide more complete results with fewer false negatives, but potentially more false positives, thereby leading to a lower confidence in the results.

As yet another example, the processing circuitry 12 may be configured to have an intermediate level of risk and, as such may not require the matching patient records to be included in each set or in one or more sets, but may, instead, require the patient records to have been identified by at least two (or some predefined number of) different patient matching strategies. Thus, the patients associated with pre-existing patient records that are included in two or more of the different sets of pre-existing patient records created by the different patient matching strategies are identified to be the same as the person with which the patient record that was received is associated. With reference to the example of FIG. 3, patient records 2, 3 and 5 would be identified as matching the patient record associated with the person that was received as each of these patient records was identified by two or more different patient matching strategies. However, patient records 1 and 4 would not be so identified since they were only identified by a single patient matching strategy. Thus, the results provided by this approach will have an intermediate level of confidence associated therewith and correspondingly have an intermediate level of false positives and false negatives.

As shown on block 46 of FIG. 2, the computer system 10 also includes means, such as the processing circuitry 12, processor 14 or the like, for defining a confidence level associated with the relationship that is defined. As described above, the processing circuit of an example embodiment may define the confidence level based upon the minimum number of different patient matching strategies that are required to identify the pre-existing patient records to be a match to the patient record associated with the person. As such, the processing circuitry of this example embodiment is configured to define the confidence level to have a direct relationship to, such as by being proportional to, the minimum number of different matching strategies that are required to separately identify the pre-existing patient record to be a match to the patient record that was received. As such, the greatest confidence level is associated with the results of an approach that requires all of the different patient matching strategies to identify the patient records that are considered to match the patient record associated with the person that was received, while the lowest confidence level is associated with the results of an approach that only requires the patient records to be identified by one or more of the different patient matching strategies in order to match the pre-existing patient record associated with the patient record of the person that was received.

Regardless of the confidence level that is defined for the results, the results generated by the method, computer system 10 and computer program product of an example embodiment that concurrently implement two or more patient matching strategies and that utilize the results of the two or more patient matching strategies to define the matching set of patient records generally provide an improvement, such as in terms of increased accuracy and completeness, relative to the use of any one of the patient matching strategies by itself. In this regard, the concurrent implementation of two or more patient matching strategies builds upon the strengths of the respective patient matching strategies, while reducing the risks associated with any one of the individual patient matching strategies. For example, the inclusiveness of a more aggressive patient matching strategy my reduce the risks associated with false negatives that are otherwise created by a more conservative patient matching strategy, while the accuracy and reliability of a more conservative patient matching strategy may reduce the risks associated with false positives that are other created by a more aggressive patient matching strategy. Since the results that are generated by the method, computer system and computer program product of an example embodiment are more reliable, both in terms of completeness and accuracy, a healthcare provider may have more confidence that they have a more complete picture of the patient's medical history and may, therefore, be able to provide improved healthcare for the patient.

In addition to generally improving the completeness and accuracy of the matching patient records that are identified, the method, computer system 10 and computer program product of an example embodiment may permit organizations, such as a health information exchange or a healthcare organization, to compare different patient matching strategies, such as the patient matching strategy that has been historically utilized by the health information exchange or a healthcare organization with other different types of patient matching strategies. Based upon this comparison including a comparison of the accuracy and completeness of the results provided by the different patient matching strategies and different combinations of the patient matching strategies, the health information exchange or other healthcare organization may better tailor the patient matching strategy or a combination of patient matching strategies that are employed in the future such that the results more accurately reflect the intentions of the health information exchange or other healthcare organization. For example, a comparison of the results provided by the different patient matching strategies and by different combinations of the patient matching strategies may permit the health information exchange or other healthcare organization to appropriately balance the processing resources that the health information exchange or other healthcare organization wishes to devote to the patient matching process on the one hand with the confidence level associated with the results provided by the patient matching strategy on the other hand.

As described above, FIG. 2 illustrates a flowchart of a computer system 10, method, and computer program product according to example embodiments of the invention. It will be understood that each block of the flowchart, and combinations of blocks in the flowchart, may be implemented by various means, such as hardware and/or a computer program product comprising one or more computer-readable mediums having computer readable program instructions stored thereon. For example, one or more of the procedures described herein may be embodied by computer program instructions of a computer program product. In this regard, the computer program product(s) which embody the procedures described herein may be stored by one or more memory devices 16 of a computing system 10 and executed by processing circuitry 12, e.g., processor 14, in the computer system. In some embodiments, the computer program instructions comprising the computer program product(s) which embody the procedures described above may be stored by memory devices of a plurality of computing devices. As will be appreciated, any such computer program product may be loaded onto a computer or other programmable apparatus to produce a machine, such that the computer program product including the instructions which execute on the computer or other programmable apparatus creates means for implementing the functions specified in the flowchart block(s). Further, the computer program product may comprise one or more computer-readable memories on which the computer program instructions may be stored such that the one or more computer-readable memories can direct a computer or other programmable apparatus to function in a particular manner, such that the computer program product comprises an article of manufacture which implements the function specified in the flowchart block(s). The computer program instructions of one or more computer program products may also be loaded onto a computer or other programmable apparatus to cause a series of operations to be performed on the computer or other programmable apparatus to produce a computer-implemented process such that the instructions which execute on the computer or other programmable apparatus implement the functions specified in the flowchart block(s).

Accordingly, blocks or steps of the flowchart support combinations of means for performing the specified functions and combinations of steps for performing the specified functions. It will also be understood that one or more blocks of the flowchart, and combinations of blocks in the flowchart, may be implemented by special purpose hardware-based computer systems which perform the specified functions or steps, or combinations of special purpose hardware and computer program product(s).

The above described functions may be carried out in many ways. For example, any suitable means for carrying out each of the functions described above may be employed to carry out embodiments of the invention. In one embodiment, a suitably configured processing circuitry 12 may provide all or a portion of the elements of the invention. In another embodiment, all or a portion of the elements of the invention may be configured by and operate under control of a computer program product. The computer program product for performing the methods of embodiments of the invention includes a computer-readable storage medium, such as the non-volatile storage medium, and computer-readable program code portions, such as a series of computer instructions, embodied in the computer-readable storage medium.

Many modifications and other embodiments of the inventions set forth herein will come to mind to one skilled in the art to which these inventions pertain having the benefit of the teachings presented in the foregoing descriptions and the associated drawings. Therefore, it is to be understood that the embodiments of the invention are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed is:

1. A method comprising:
    implementing a plurality of different matching strategies to separately associate a record associated with a person and pre-existing records, wherein implementing the plurality of different matching strategies comprises:
        implementing a first matching strategy to associate a record associated with a person and pre-existing records, wherein implementing the first matching strategy comprises:
            identifying, with processing circuitry, one or more links between the record associated with the person and pre-existing records, wherein identifying one or more links comprises identifying one or more links based upon an analysis pursuant to the first matching strategy of demographic attributes of the person and respective individuals associated with the pre-existing records; and
            associating the record associated with the person and a first set of pre-existing records based upon the first matching strategy including the one or more links identified thereby; and
        implementing a second matching strategy, different than the first matching strategy, to associate the record associated with the person and pre-existing records, wherein implementing the second matching strategy comprises:
            identifying, with the processing circuitry, one or more links between the record associated with the person and pre-existing records, wherein identifying one or more links comprises identifying one or more links based upon an analysis pursuant to the second matching strategy of demographic attributes of the person and the respective individuals associated with the pre-existing records, wherein the second matching strategy differs from the first matching strategy as a result of reliance by the second matching strategy upon one or more of consideration of different demographic attributes, application of different weights to the demographic attributes or use of a different match threshold with respect to identification of a link than the first matching strategy; and
            associating the record associated with the person and a second set of pre-existing records, different than the first set of pre-existing records, based upon the second matching strategy including the one or more links identified thereby, wherein the first and second sets are different in terms of one or more of the pre-existing records included in the first and second sets or a number of pre-existing records included in the first and second sets;
    based upon a combination of results from both the first and second matching strategies, defining a relationship between the person and respective individuals associated with one or more of the pre-existing records of the first set and the second set of pre-existing records as defined by the combination of the first and second matching strategies, respectively; and
    providing at least a portion of a medical history of the person for use by a healthcare professional based upon the one or more pre-existing records of the first set and the second set of pre-existing records as defined by the combination of the first and second matching strategies, respectively.

2. A method according to claim 1 wherein implementing the first and second matching strategies comprises identifying one or more links between the record associated with the person and pre-existing records utilizing a first match threshold in conjunction with the analysis pursuant to the first matching strategy and a second match threshold, different than the first match threshold, in conjunction with the analysis pursuant to the second matching strategy.

3. A method according to claim 1 wherein implementing the first and second matching strategies comprises identifying one or more links between the record associated with the person and pre-existing records with demographic attributes that are found to satisfy the match threshold being differently weighted pursuant to the first matching strategy than pursuant to the second matching strategy.

4. A method according to claim 1 wherein implementing the plurality of matching strategies comprises concurrently implementing the plurality of matching strategies.

5. A method according to claim 1 further comprising identifying each link between the record associated with the person and pre-existing records that is identified by any one or more of the plurality of matching strategies based upon the respective matching strategy via which the link was identified.

6. A method according to claim 1 further comprising defining a confidence level associated with the relationship between the person and respective individuals associated with at least one of the first set or the second set of pre-existing records, wherein the confidence level is dependent upon whether the respective individuals are associated with only one of the first set or the second set of pre-existing records or are associated with both of the first set and the second set of pre-existing records.

7. A method according to claim 1 further comprising receiving a selection of one of the first or second matching strategies or a modification of at least one of the first or second matching strategies based upon an evaluation of the first and second sets of pre-existing records as defined by the first and second matching strategies, respectively.

8. A computer system comprising a processing circuitry configured to:
    implement a plurality of different matching strategies to separately associate a record associated with a person and pre-existing records, wherein the processing circuitry is configured to implement the plurality of different matching strategies by:
  implementing a first matching strategy to associate a record associated with a person and pre-existing records, wherein the processing circuitry is configured to implement the first matching strategy by:
    identifying one or more links between the record associated with the person and pre-existing records, wherein identifying one or more links comprises identifying one or more links based upon an analysis pursuant to the first matching strategy of demographic attributes of the person and respective individuals associated with the pre-existing records; and
    associating the record associated with the person and a first set of pre-existing records based upon the first matching strategy including the one or more links identified thereby; and
  implementing a second matching strategy, different than the first matching strategy, to associate the record associated with the person and pre-existing records, wherein the processing circuitry is configured to implement the second matching strategy by:
    identifying one or more links between the record associated with the person and pre-existing records, wherein identifying one or more links comprises identifying one or more links based upon an analysis pursuant to the second matching strategy of demographic attributes of the person and the respective individuals associated with the pre-existing records, wherein the second matching strategy differs from the first matching strategy as a result of reliance by the second matching strategy upon one or more of consideration of different demographic attributes, application of different weights to the demographic attributes or use of a different match threshold with respect to identification of a link than the first matching strategy; and
    associating the record associated with the person and a second set of pre-existing records, different than the first set of pre-existing records, based upon the second matching strategy including the one or more links identified thereby, wherein the first and second sets are different in terms of one or more of the pre-existing records included in the first and second sets or a number of pre-existing records included in the first and second sets;
  based upon a combination of results from both the first and second matching strategies, define a relationship between the person and respective individuals associated with one or more of the pre-existing records of the first set and the second set of pre-existing records as defined by the combination of the first and second matching strategies, respectively; and
  provide at least a portion of a medical history of the person for use by a healthcare professional based upon the one or more pre-existing records of the first set and the second set of pre-existing records as defined by the combination of the first and second matching strategies, respectively.

9. A computer system according to claim 8 wherein the processing circuitry is configured to implement the first and second matching strategies by identifying one or more links between the record associated with the person and pre-existing records utilizing a first match threshold in conjunction with the analysis pursuant to the first matching strategy and a second match threshold, different than the first match threshold, in conjunction with the analysis pursuant to the second matching strategy.

10. A computer system according to claim 8 wherein the processing circuitry is configured to implement the first and second matching strategies by identifying one or more links between the record associated with the person and pre-existing records with demographic attributes that are found to satisfy the match threshold being differently weighted pursuant to the first matching strategy than pursuant to the second matching strategy.

11. A computer system according to claim 8 wherein the processing circuitry is configured to implement the plurality of matching strategies by concurrently implementing the plurality of matching strategies.

12. A computer system according to claim 8 wherein the processing circuitry is further configured to identify each link between the record associated with the person and pre-existing records that is identified by any one or more of the plurality of matching strategies based upon the respective matching strategy via which the link was identified.

13. A computer system according to claim 8 wherein the processing circuitry is further configured to define a confidence level associated with the relationship between the person and respective individuals associated with at least one of the first set or the second set of pre-existing records, wherein the confidence level is dependent upon whether the respective individuals are associated with only one of the first set or the second set of pre-existing records or are associated with both of the first set and the second set of pre-existing records.

14. A computer system according to claim 8 wherein the processing circuitry is further configured receive a selection of one of the first or second matching strategies or a modification of at least one of the first or second matching strategies based upon an evaluation of the first and second sets of pre-existing records as defined by the first and second matching strategies, respectively.

15. A computer program product comprising a non-transitory computer readable storage medium having program code portions stored thereon, the program code portions configured, upon execution, to:
  implement a plurality of different matching strategies to separately associate a record associated with a person and pre-existing records, wherein the program code portions are configured to implement the plurality of different matching strategies by:
    implementing a first matching strategy to associate a record associated with a person and pre-existing records, wherein the program code portions are configured to implement the first matching strategy by:
      identifying one or more links between the record associated with the person and pre-existing records, wherein identifying one or more links comprises identifying one or more links based upon an analysis pursuant to the first matching strategy of demographic attributes of the person and respective individuals associated with the pre-existing records; and
      associating the record associated with the person and a first set of pre-existing records based upon the first matching strategy including the one or more links identified thereby; and
    implementing a second matching strategy, different than the first matching strategy, to associate the record associated with the person and pre-existing records, wherein the program code portions are configured to implement the second matching strategy by:

identifying one or more links between the record associated with the person and pre-existing records, wherein identifying one or more links comprises identifying one or more links based upon an analysis pursuant to the second matching strategy of demographic attributes of the person and the respective individuals associated with the pre-existing records, wherein the second matching strategy differs from the first matching strategy as a result of reliance by the second matching strategy upon one or more of consideration of different demographic attributes, application of different weights to the demographic attributes or use of a different match threshold with respect to identification of a link than the first matching strategy; and associating the record associated with the person and a second set of pre-existing records, different than the first set of pre-existing records, based upon the second matching strategy including the one or more links identified thereby, wherein the first and second sets are different in terms of one or more of the pre-existing records included in the first and second sets or a number of pre-existing records included in the first and second sets;

based upon a combination of results from both the first and second matching strategies, define a relationship between the person and respective individuals associated with one or more of the pre-existing records of the first set and the second set of pre-existing records as defined by the combination of the first and second matching strategies, respectively; and provide at least a portion of a medical history of the person for use by a healthcare professional based upon the one or more pre-existing records of the first set and the second set of pre-existing records as defined by the combination of the first and second matching strategies, respectively.

16. A computer program product according to claim 15 wherein the program code portions configured to implement the first and second matching strategies comprise program code portions configured to identify one or more links between the record associated with the person and pre-existing records utilizing a first match threshold in conjunction with the analysis pursuant to the first matching strategy and a second match threshold, different than the first match threshold, in conjunction with the analysis pursuant to the second matching strategy.

17. A computer program product according to claim 15 wherein the program code portions configured to implement the first and second matching strategies comprise the program code portions configured to identify one or more links between the record associated with the person and pre-existing records with demographic attributes that are found to satisfy the match threshold being differently weighted pursuant to the first matching strategy than pursuant to the second matching strategy.

18. A computer program product according to claim 15 wherein the program code portions configured to implement the plurality of matching strategies comprise program code portions configured to concurrently implement the plurality of matching strategies.

19. A computer program product according to claim 15 wherein the program code portions are further configured to identify each link between the record associated with the person and pre-existing records that is identified by any one or more of the plurality of matching strategies based upon the respective matching strategy via which the link was identified.

20. A computer program product according to claim 15 wherein the program code portions are further configured to define a confidence level associated with the relationship between the person and respective individuals associated with at least one of the first set or the second set of pre-existing records, wherein the confidence level is dependent upon whether the respective individuals are associated with only one of the first set or the second set of pre-existing records or are associated with both of the first set and the second set of pre-existing records.

* * * * *